(12) United States Patent
Lazarev et al.

(10) Patent No.: US 6,483,891 B1
(45) Date of Patent: Nov. 19, 2002

(54) REDUCED-ANGLE MAMMOGRAPHY DEVICE AND VARIANTS

(75) Inventors: Pavel Ivanovich Lazarev, Moscow (RU); Oleg Valentinovich Komardin, Moscow (RU)

(73) Assignee: Quanta Vision, Inc., San Mateo, CA (US)

( * ) Notice: Subject to any disclaimer, the term of this patent is extended or adjusted under 35 U.S.C. 154(b) by 0 days.

(21) Appl. No.: 09/787,349

(22) PCT Filed: Sep. 13, 1999

(86) PCT No.: PCT/RU99/00333
§ 371 (c)(1),
(2), (4) Date: Mar. 16, 2001

(87) PCT Pub. No.: WO00/15112
PCT Pub. Date: Mar. 23, 2000

(30) Foreign Application Priority Data

Sep. 17, 1998 (RU) .......................................... 98117703

(51) Int. Cl.$^7$ ................................................ A61B 6/04
(52) U.S. Cl. .............................. 378/37; 378/86; 378/88; 378/90
(58) Field of Search .............................. 378/37, 86, 87, 378/88, 89, 90, 195, 196, 197

(56) References Cited

U.S. PATENT DOCUMENTS

| | | |
|---|---|---|
| 3,973,126 A | 8/1976 | Redington et al. |
| 4,651,002 A | 3/1987 | Anno |
| 4,751,722 A | 6/1988 | Harding et al. |
| 4,962,515 A | 10/1990 | Kopans |
| 4,969,174 A | 11/1990 | Schied et al. |
| 5,239,568 A | 8/1993 | Grenier |
| 5,394,454 A | * 2/1995 | Harding ........................ 378/86 |
| 5,426,685 A | 6/1995 | Pellegrino et al. |
| 5,594,769 A | * 1/1997 | Pellegrino ..................... 378/37 |
| 6,054,712 A | * 4/2000 | Komardin et al. ...... 250/363.06 |
| 6,122,344 A | * 9/2000 | Beevor ......................... 378/88 |
| 6,175,117 B1 | * 1/2001 | Komardin et al. ...... 250/363.06 |

FOREIGN PATENT DOCUMENTS

EP    0 153 750    9/1985

* cited by examiner

Primary Examiner—David P. Porta
Assistant Examiner—Allen C. Ho
(74) Attorney, Agent, or Firm—Burns, Doane, Swecker & Mathis, L.L.P.

(57) ABSTRACT

The invention relates to the mammography devices based on registration of a reduced-angle coherently scattered radiation when an object is rayed by a penetrating radiation. Registration of the radiation coherently scattered by an object allows to produce an image of an object in the form of distribution of its structural characteristics. The device comprises a system for forming a directed on a tested object, narrow small-divergence beams, or a beam, having the same characteristics, and a system for extracting the radiation that is coherently scattered in small angles by an object. The invention proposes versions of a device that also provide for registration of the radiation passed through an object to make allowance for its thickness so that to obviate the necessity to compress the breast. The device allows to carry out relative movements of an object and system of irradiation-registration, as well as irradiate an object at different angles and by a number of radiation sources simultaneously. The possibility to register the coherently scattered radiation in ultra-small angles within the range of several angular seconds to 0.5 degree, and also the possibility to form the primary radiation beam having a sharp boundary are provided as well.

7 Claims, 6 Drawing Sheets

REDUCED-ANGLE MAMMOGRAPHY DEVICE AND VARIANTS

FIELD OF THE INVENTION

The proposed invention relates to devices for producing an object image using reduced-angle scattering of a penetrating radiation, namely—to mammography devices that determine changes in the tissue structure. The invention can be suitably used in medical application for diagnosing the cancer cases of mammary glands at an early stage of a disease.

PRIOR ART

The known mammography devices are generally based on the principle that different substances, being subjected to raying, exhibit different properties of absorbing the X-ray radiation. The intensity of a radiation passed through an object and forming its projection image is determined by absorption property (absorption coefficient) of the substances constituting the object and by their thickness in the raying direction. To provide a quality image, it is necessary that a whole object would have the same thickness in the raying direction. The known devices provide said feature by compressing mammary gland to desired (or allowable) size (U.S. Pat. No. 4,962,515, Sep. 10, 1996). However, such compression results in that a patient feels a pain and discomfort.

Another method of compensating a variable thickness of an object consists in placing mammary gland in a cylindrical vessel filled with an immersion liquid that has the same X-ray absorption coefficient as the gland. Such approach is used, for example, in mammary gland tomography (U.S. Pat. No. 3,973,126, Mar. 08, 1976). For producing one projection of mammary gland, a similar result can be attained by introducing plate-shaped attenuating filters (made of aluminium or other material) into the raying zone, in particular in cases of studying the subsurface subcutaneous areas of mammary gland (U.S. Pat. No. 4,969,174, Jun. 11, 1990). There is no need of any compression in the use of this approach for producing an image.

Another technique to obviate the need to compress mammary gland is provided when an image is produced by scanning of an object with a narrow X-ray beam. In the device of such approach (U.S. Pat No. 4,969,174, Jun. 11, 1990), an image is produced on a photographic film, under which film rows of X-ray detectors are arranged. The detectors determine the time required for exposing the photographic film for each of the raying beam position. A signal from the detector is supplied to a scanning system control unit, and allowance for various breast thickness was made for by different rates of the beam movement. In this system, scanning is performed along the breast axis.

In the devices based on principles of the conventional absorption X-raying, i.e. on registration of intensity distribution of the radiation passed through a rayed object, the scattered radiation is a parasitic phenomenon that creates a background and affects the image contrast. To overcome the scattered radiation, said radiation is registered separately using a collimating grid and a filter, and the registered signal is deducted as the background from the total signal produced when an object is rayed (U.S. Pat. No. 4,651,002). The scattering pattern is measured integrally, and a filter is implemented as a movable member, the scattered radiation being measured at large angles.

An essential index of performance of an X-ray mammography device is the irradiation dose absorbed by a patient during checking. A partial decrease of the irradiation dose is provided by a decreased thickness of the checked object (breast compression).

Another technique to reduce the irradiation dose is selection of the X-ray radiation parameters. For example, application of replaceable filters allows to select the radiation hardness for each patient (U.S. Pat. No. 4,969,174, Jun. 11, 1990).

When a patient's breast is scanned by an X-ray beam, the irradiation dose is decreased by monitoring of the passed radiation by detectors. Then the breast raying (scanning) is selected to be optimal so that to minimize the patient irradiation dose and produce a clear image.

In all above-discussed devices, a patient usually is positioned in the standing or inclined position, and mammary gland is fixed normally to the patient's body.

All above-discussed devices are based on the principle of producing images as the difference in absorption of the rays passing through a patient's mammary gland via different paths. As coefficients of absorption by the breast soft tissues have only a slight difference, so it is difficult to determine minor changes in tissues in early stages of a disease.

The mentioned drawbacks are avoided by using a method of registering the radiation coherently scattered by an object for producing an image. U.S. Pat. No. 4,751,722, G 01 N 23/22, 1988, describes a device, wherein the radiation passed through an object and the angular distribution of the coherently scattered radiation lying at angles of 1° to 12° in relation to the incident beam direction are registered simultaneously. As said patent discloses, the main portion of the elastically-scattered radiation is concentrated in the angles less than 12°, and the scattered radiation has a characteristic angular relationship having pronounced maxima, the location of which maxima is determined both by the irradiated substance itself and the incident radiation energy. As distribution of intensity of the coherently scattered radiation within small angles depends on the molecular structure of a substance, then different substances having the same absorptive capacity may differ regarding the distribution of intensity of the coherent radiation angular scattering being intrinsic to each substance. In case an object is heterogeneous, i.e. consists of different substances, then intensity of a radiation scattered at each particular angle is constituted by intensities of the rays scattered by different substances on the path of propagation of a penetrating radiation beam. This patent proposes to use a narrow collimated beam of a monochromatic or polychromatic radiation for irradiating an object. A detecting system has the resolution property both for energy and coordinate (scattering angle). Said device comprises an X-ray source having a diaphragm that forms a primary radiation beam such that said beam has a small cross-section in the plane normal to the beam propagation direction. Having passed through a tested object, the beam is registered by a row of detectors, one of which is positioned such that it registers the primary beam passed through an object (or the tested object area), the other detectors being positioned in the plane normal to the ray plane, or on a straight line in said plane, and oriented such that they register only the coherently scattered radiation. Further, each detector of said detector row registers the radiation that is scattered at a certain angle.

The above-described device has a relatively low sensitivity to the radiation scattered in immediate vicinity of the primary beam, because the primary beam radiation intensity considerably exceeds that of the scattered radiation and hinders the registration thereof. Further, the radiation intensity sharply falls when the scattering angle grows, thus the coherently scattered radiation intensity within the range of 1–12 degrees is low, hence the sufficiently high irradiation doses and a long exposure are required for testing an object.

DISCLOSURE OF THE INVENTION

The object of the invention is to provide devices that are more sensitive to registration of the coherent scattered radiation in ultra-small angles (tens of seconds to one degree), which will allow to reduce the radiation dose in testing of an object. Attainment of said object will allow to avoid compression of breast, i.e. avoid patient's pain and discomfort.

The main part of coherently scattered radiation is concentrated in the central diffraction peak that is situated in the scattering angles of 0 to 1 degree relative to the primary beam incidence direction. In this angular range concentrated is the radiation coherently scattered by heterogeneities of the object electronic structure, which heterogeneities have characteristic dimensions of several hundreds to tens thousands Angstrom, which corresponds to structure of many biological objects. This is the reason to measure distribution of coherently scattered radiation just within this angular interval. The measurement angular range depends on wavelength of the used radiation and structural properties of a material, and can be within the range of several angular seconds to 1 degree relative to the incident beam. The invention proposes to use the dark-field measurement technique, where in the absence of a tested object a detector registers only the background signal, and when said object is present it registers only the scattered radiation.

For producing an image representing distribution of the tissue structural characteristics in an object, the invention proposes different embodiments of mammography devices that provide registration of the radiation angular distribution in said angular interval, or that of the radiation integral intensity within the angular interval of one angular second to 0.5 degree; as well as simultaneous registration of the radiation passed through a tested object. In reference to the nature of the scattered radiation angular distribution curve and a value of the integral signal of the coherently scattered radiation in said angular interval, the structure of a tested object can be ascertained.

The first embodiment of the device that achieves the above-stated object, is a device intended for reduced-angle mammography, comprising a source of a penetrating radiation, collimator that forms a radiant flux incident upon an object in the form of narrow small-divergence fan-shaped beams (or a beam), a spatial filter disposed downstream of the object and a position-sensitive detector. The spatial filter is positioned to overlap the radiation primary beam and provide passing of the coherent radiation scattered in ultra-small angles near the primary beam boundaries, to a detector. The proposed system that consists of a source, collimator, spatial filter, detector, is fitted to a frame capable of moving relative to a tested object in the plane normal to the beam plane. The frame is adapted to rotate with respect to the object axis to ray the same from different directions. In some cases, the possibility to move a patient relative to a fixed frame is provided for.

In the second embodiment of the device: a frame having a source, collimator, spatial filter and detector is capable of swinging about an object in the plane normal to the beam plane for the purpose to scan the object.

The third embodiment of the device is also proposed, wherein it comprises at least another radiation source having a collimator, spatial filter, position-sensitive detector which are identical to the first ones. In this embodiment, each system, consisting of a source, collimator, spatial filter, detector, is capable of moving one after another, opposite to one another and in two mutually perpendicular directions in the plane normal to the beam plane.

In any of the proposed embodiments, a collimator can be implemented in the form of one slit or in the form of a regular periodic structure being the radiation-transparent areas in the form of slits, and the opaque areas interleaved therewith. Use of a multi-slit collimator that forms a number of small-divergence beams allows a more efficient use of the source radiation. The rays formed by the collimator overlap a separate strip in the object projection. The spatial filter in this case is a collimator-like regular periodic structure, wherein the areas corresponding to the collimator transparent areas are made of a material opaque to a penetrating radiation such that the filter opaque areas overlap the collimator transparent areas. Further, size of slits, and structural period of the collimator, and size of transparent areas of the spatial filter must provide registration of only the radiation coherently scattered at small angles by the position-sensitive detector. The collimator must form the beams having a width and divergence providing the possibility to register the radiation scattered within a small-angle range, i.e. so that any ray scattered by an object at a small angle will transgress the primary beam boundaries in the registration zone. Further, the structural period of the collimator must by such that adjacent beams will not overlap one another in the detector plane. To register the source's primary radiation that passed through an object, additional elements of the position-sensitive detector are positioned on the filter opaque areas.

In any of the proposed embodiments, a translucent spatial filter that overlaps the radiation primary beam passed through an object and reduces its intensity at least to the level of the scattered radiation intensity preferably less than a number of times, can be used also. This will allow to improve sensitivity to the radiation scattered in immediate vicinity of the primary beam and, consequently, further reduce the patient irradiation dose.

For the purpose of a more substantial decrease of the patient irradiation dose and to make the exposure period briefer, the possibility to register the scattered radiation integral flux in a particular angular range is also provided; the highest contrast of an image (contrast is obtained by a difference in the integral intensity of the radiation scattered by each of the irradiated substances) is to be achieved in registration of the coherently scattered radiation within the angular interval of several seconds to 0.5 degree. Changes in the signal level relative to the whole flux of the coherently scattered radiation will be determined by the scattering function of a given object. In this case it is preferable to use one-coodinate position-sensitive detectors implemented as linear gas meters, and register the scattered radiation in the quantum counting mode.

An improvement of sensitivity to the radiation scattered in immediate vicinity of the primary beam can be attained by forming a beam having a sharp boundary and by an high precision of positioning of the spatial filter with respect to the collimator. For achieving this result, in the device, the collimator and spatial filter are implemented as a single unit whose entry portion facing the radiation source is a Kratky collimator having input and output diaphragms. The upper edge of the input diaphragm is situated in the plane that is common with the nether edge of the output diaphragm and the upper edge of the spatial filter; a free space is provided between the collimator and spatial filter, which space is intended for movement of an object.

An X-ray source having radiation hardness and intensity that provide a minimal patient irradiation dose, while producing a quality image, is selected as the source. Size of the radiation source focal spot depends on the <<collimator-spatial filter>> system used in a particular device. The <<collimator-spatial filter>> elements are interrelated and determine all operation parameters of the proposed device.

An example of design of a device based on the described principle and its basic parameters is given below.

The device includes: an X-ray source, collimator (or a unit of collimators), patient table equipped with a system of relative movement of the device and patient, spatial filter and position-sensitive detector; and also a system of registration, analysis and imaging of data, and a system of adjusting the device and monitoring its parameters. The devices allows to produce an image of a tested object in the rays scattered at small angles, spatial resolution of details of an object being about 100 $\mu$m. The intended contrast in such arrangement must 1.5–4 times exceed that obtained in conventional mammography images produced by different absorptivity of X-ray radiation by an object. Total analysis time does not exceed 1 min. The dose absorbed by a patient during the whole testing time will not be over 4 mGy. Below are given parameters of the device elements that permit to achieve these results.

X-ray Source

Used is a standard source of pulse X-ray radiation, having a rotating molybdenum anode. Voltage across the X-ray tube is selected within the range of 20–40 kV, the pitch being 0.5 kV, depending of the tested object parameters. Value of current in such arrangement is 16 to 120 mA. Size of the source focal spot is 0.3×0.3 mm. The distance from the source focal spot to the collimator input is 100 mm.

Collimator

The used collimator is implemented as a Kratky collimator. Height of the collimator input slit is 80 $\mu$m, length being 85 mm. Total length of the collimator is 100 mm. The collimator forms a narrow fan-shaped X-ray beam having at least one sharp boundary. Size of the X-ray beam in the object plane is 0.1×180 mm.

Spatial Filter

The spatial filter must be implemented of a material that well absorbs and weakly scatters the X-ray radiation. The distance from a tested object to the spatial filter is 500 mm. The plate of which the spatial filter is implemented must have extremely even working edges across the entire width of the X-ray beam.

Space-Sensitive Detector

The space-sensitive detector is a two-dimension array of the elements sensitive to X-ray radiation, for example a CCD-array. The detector is to be positioned immediately downstream of the spatial filter. Dimensions of the space-sensitive detector: 5×420 mm, size of pixels being 100 $\mu$m. Such arrangement will provide registration of distribution of intensity of the scattered radiation with angular resolution of 40 angular seconds.

BRIEF DESCRIPTION OF DRAWINGS

The invention essence is explained by drawings, in which.

EMBODIMENTS OF THE INVENTION

Figure 1:
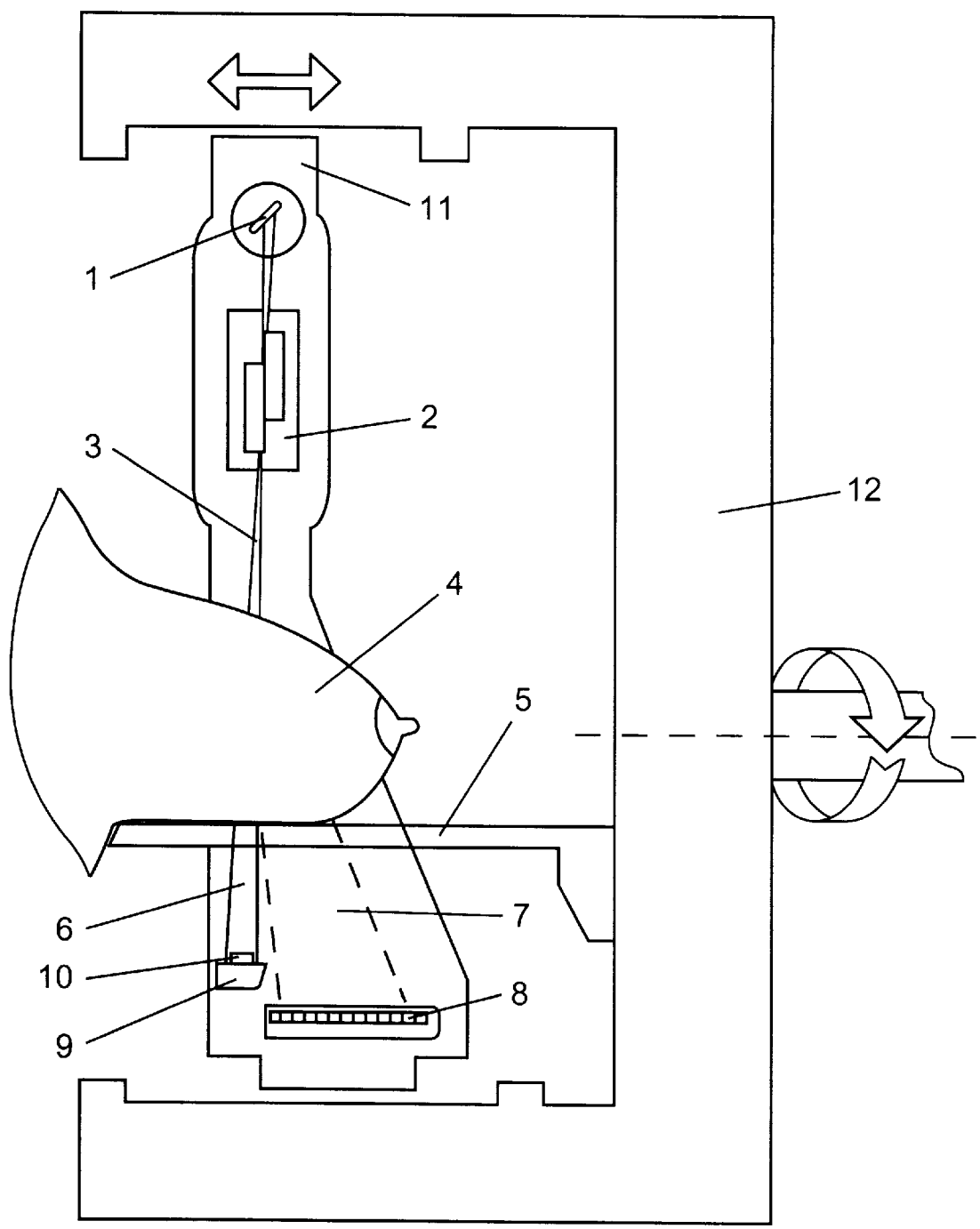
FIG. 1 shows an embodiment of a mammograph, wherein the system, consisting of a source, collimator, spatial filter, detector, is adapted to move relative to an object in the plane normal to the beam plane, and also rotate relative to the object while being fixed in each position so that to ray a selected area of an object at different angles.

Devices are operated as follows. Radiation from source 1 of a penetrating radiation, for example, X-ray tube, is formed using collimator 2 into planar fan-shaped beam 3 (FIG. 1), or a number of fan-shaped beams (as in FIG. 2), and is directed to tested object 4 disposed on holder 5. On the path of the passed 6 through the object and scattered 7 radiation, positioned is position-sensitive detector 8 in the form of an array of radiation-sensitive elements intended for registration of the reduced-angle scattering, and also radiation-opaque filter 9 whereon positioned is detector 10 for registration of the radiation passed through the object. The registration system can be arranged in another way: filter 9 can be translucent, detector 10 can be disposed downstream of the filter. All instruments intended to form the radiation field and perform registration are disposed on frame 11 installed in turn on base 12. The frame on guides is moved in the direction normal to the radiation beam plane to scan the object, and the base is adapted to rotate as being fixed at each setting so that to provide irradiation of the tested object at various angles.

Figure 2:
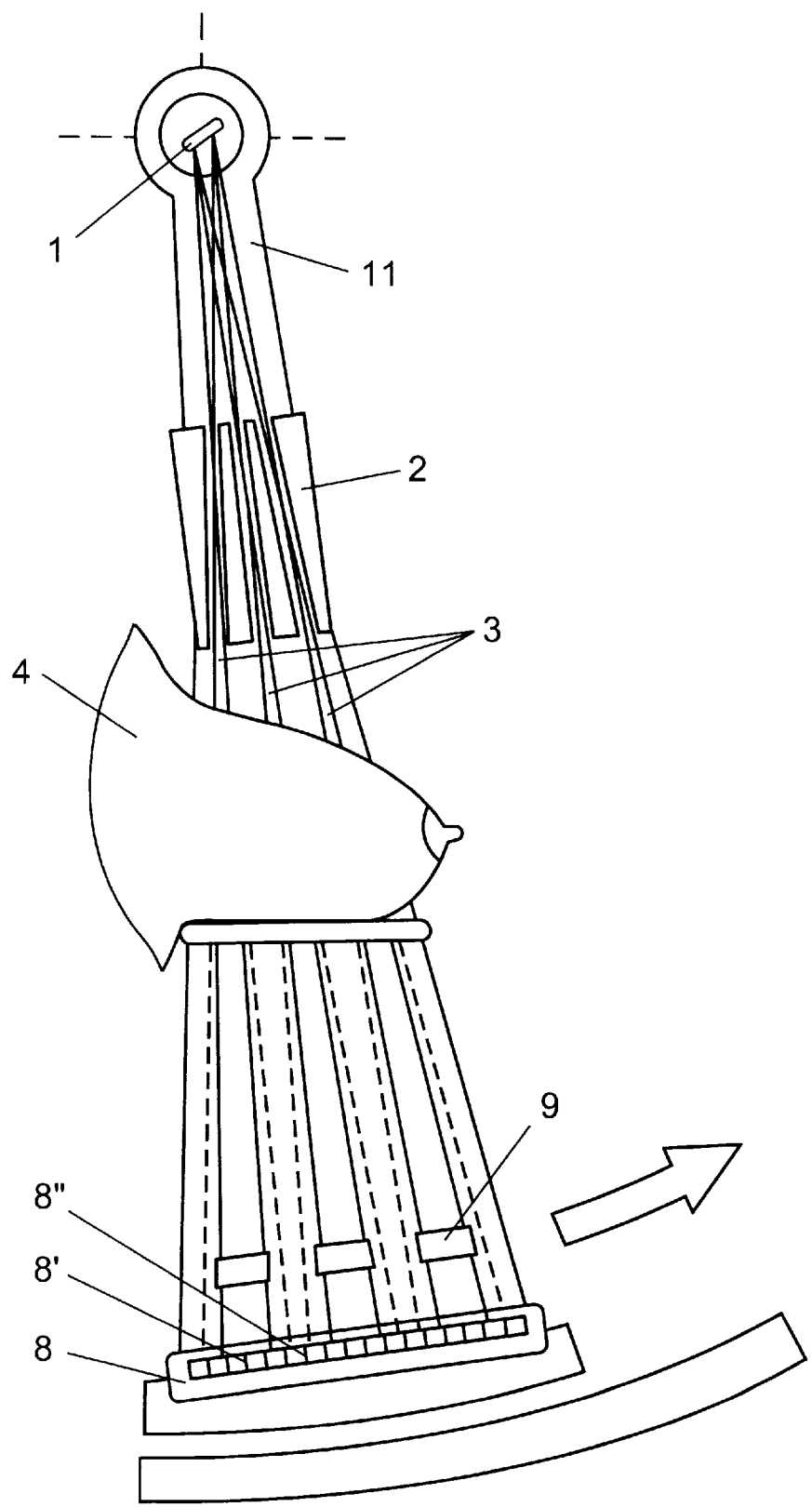
FIG. 2 shows the second embodiment of the device, wherein said system is adapted to rotate about an object in the plane normal to the beam plane.

FIG. 2 shows the embodiment of the proposed device wherein frame 11 is adapted to swing relative to the object in the arrowed direction relative to the axis extending through the source focal spot. In this embodiment: 2 is a multi-slit collimator that forms several fan-shaped beams 3. Filter 9 that overlaps the radiation primary beam, passed through the object, consists of identical areas, number of which areas is equal to that of the collimator slits, and can be implemented as being translucent to the incident radiation. Then portion 8' of detectors 8 of the detector array, positioned downstream of the filters, registers the radiation passed through the object and attenuated to the scattered radiation level, and remaining portion 8" of the detectors registers the radiation scattered at small angles. Filter 9 can also be opaque. In this case, upstream of the filter (or thereon) positioned are detectors that register the primary beam that passed through the object, as shown in FIG. 1.

Figure 3:
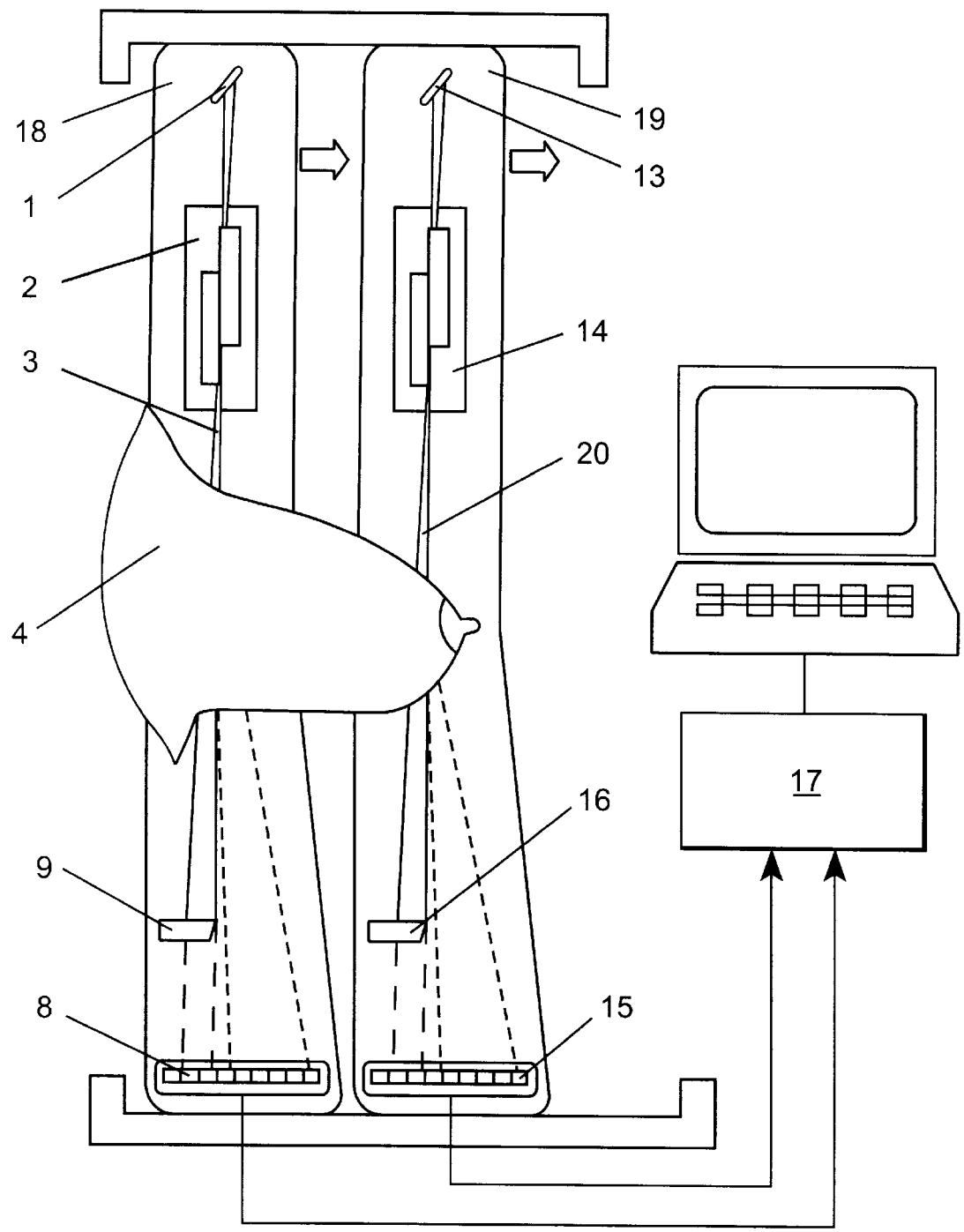
FIG. 3 shows a device having two identical sources with collimators and, respectively, with two filters and position-sensitive detectors.

FIG. 3 shows the third embodiment of the device. An object is rayed with two penetrating radiation sources 1 and 13. Collimators 2 and 14 form two fan-shaped beams to irradiate the object. Translucent filters 9 and 16 reduce intensity of the radiation passed through the object to a magnitude of the same order as the scattered radiation. Two arrays of detectors 8 and 15 register the entire radiation downstream of the object; a portion of the detector elements, that is disposed in the primary beam downstream of the translucent filter, measures the passed radiation, and the remaining portion of the detector elements measures the reduced-angle radiation coherently scattered at respective angles. The registered signals are supplied to information processing unit 17. Each of the system, consisting of a source, collimator, spatial filter, detector, is arranged on frames 18 and 19, respectively, adapted to move one after another in the plane normal to that of radiation beams 3 and 20.

Figure 4:
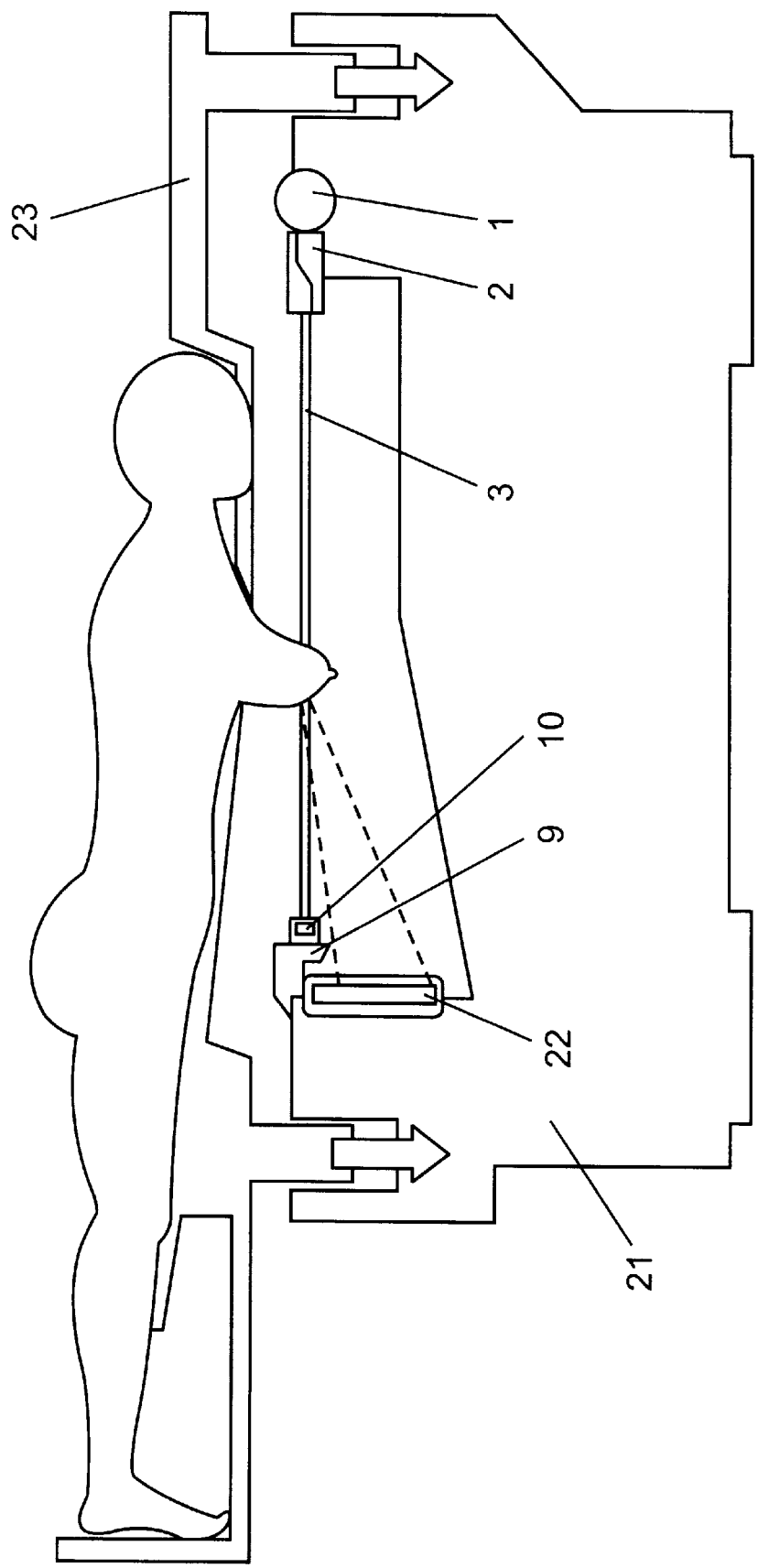
FIG. 4 shows a device that provides for movement of a patient relative to the system, consisting of a source, collimator, spatial filter, detector, wherein an integral detector is used as a detector for registration of the scattered radiation, which integral detector collects the whole scattered radiation within a predetermined angular interval.

FIG. 4 shows the device wherein a patient is moved relative to base 21, whereon positioned are source 1 with collimator 2, spatial filter 9 and detector 22. Space-sensitive detector 22 is a one-coordinate linear detector having resolution along the beam 3 plane. This device uses opaque filter 9, whereon positioned is detector 10 that registers intensity of the radiation passed through the object. Table 23, whereon a patient is to be positioned, is equipped with means for movement relative to base 21 in the plane normal to the beam 3 plane.

Figure 5A:
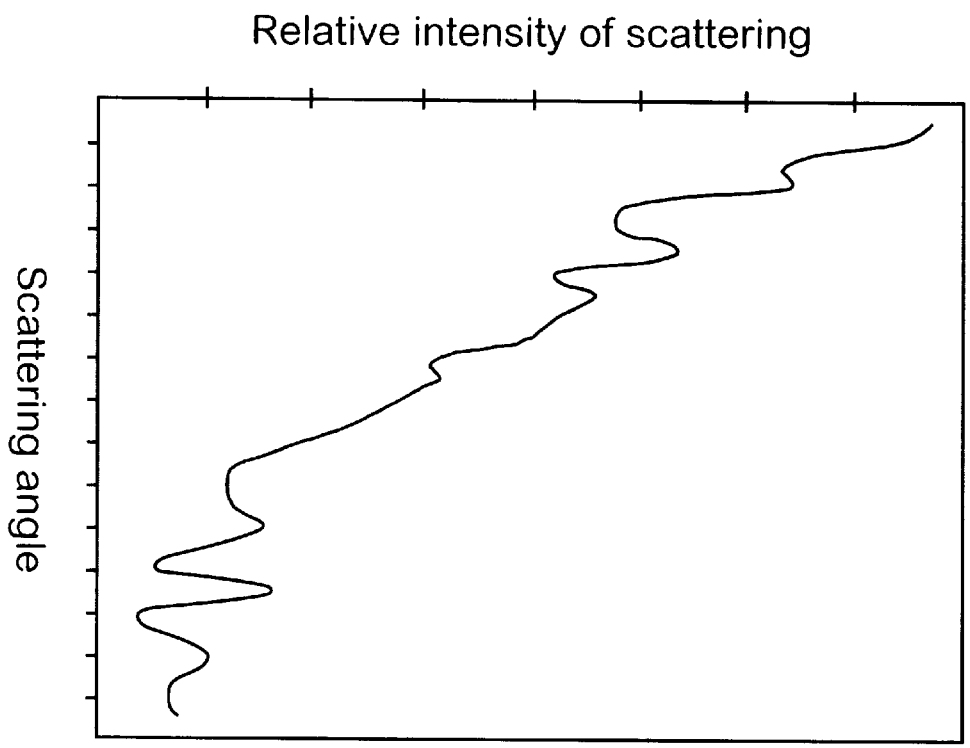
FIG. 5 shows distribution of intensity of the coherently scattered radiation by different tissues of mammary gland.
Figure 5B:
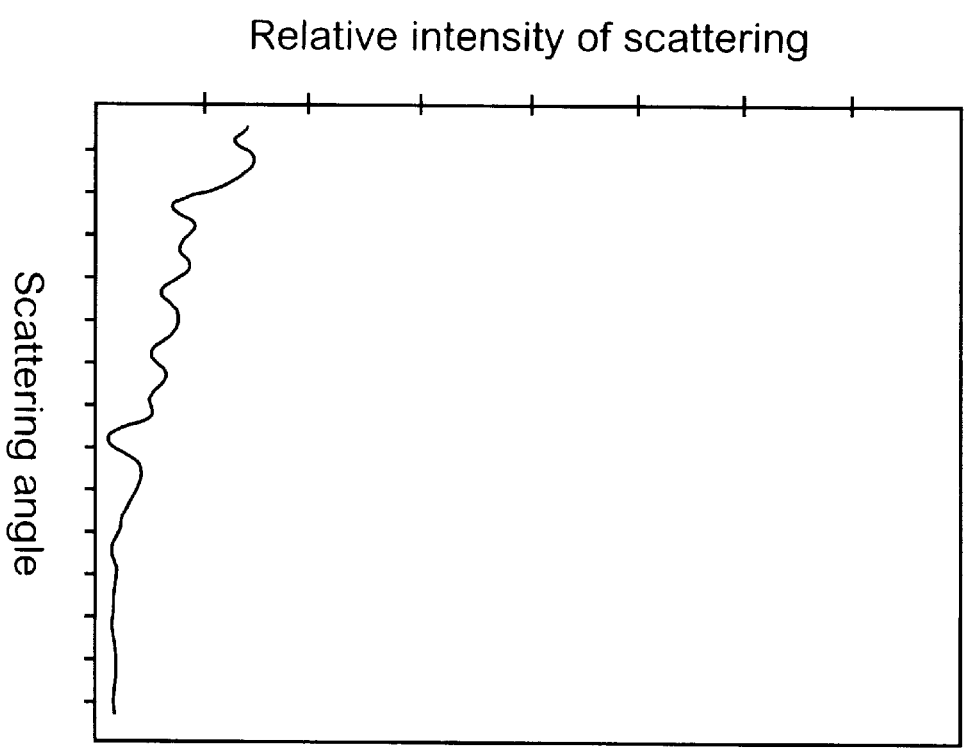

FIG. 5 shows difference of scattering properties of the healthy tissue of mammary gland and that of a cancer tumour. The scattering function of any substance is determined by its structure and is the <<identity card>> of a given substance and its condition, and can be used to identify them. Thus, by comparing the measured distribution of intensity of the reduced-angle coherently scattered radiation and the integral value of intensity of the radiation scattered within a specific angular range with the results stored in a database for the control objects, a particular tissue that has a scattering property resulting in such angular distribution can be determined. FIG. 5*a* shows the curve of distribution of intensity of reduced-angle scattering of radiation, which scattering is effected by the cancer tumour tissue, and FIG. 5*b* shows that of the adjacent unaffected tissue of mammary gland.

Figure 6:
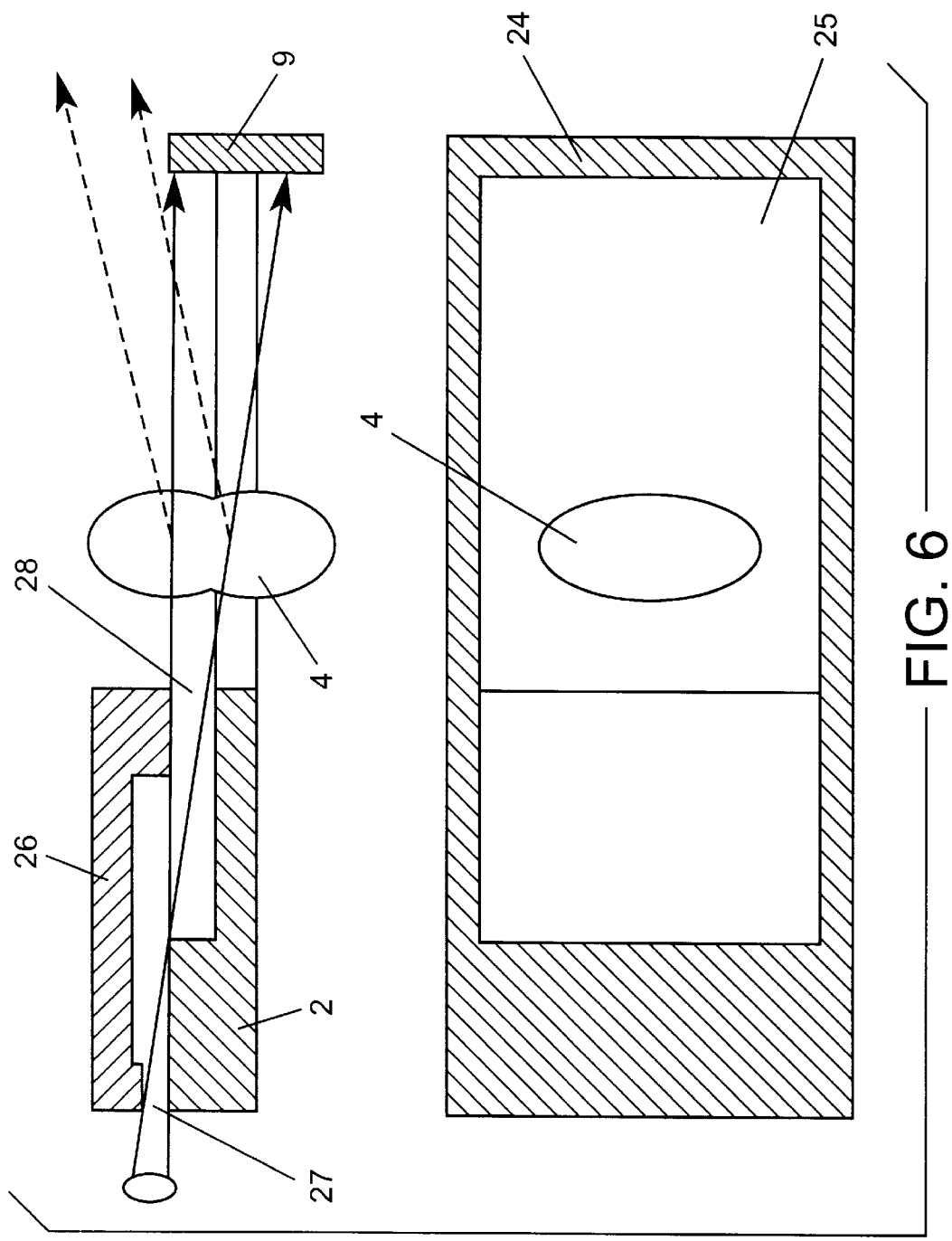
FIG. 6 shows a possible implementation of a portion of the device, which portion is intended for forming a beam of radiation that rays an object, and for extracting the radiation scattered by an object, in accordance with the invention.

FIG. 6 shows a portion of the device, which portion, in any of the embodiments, allows to form a beam of radiation that rays an object and to extract the radiation scattered by the object. This portion of the device is implemented in the form of frame 24, in which frame space 25 is intended for accommodating tested object 4. The upper portion of collimator 2 is implemented as unit 26 having stepped cuts that form input 27 and output 28 diaphragms, which diaphragms form a fan-shaped beam having a sharp upper boundary (Kratky collimator). Depending on the testing purpose, number of diaphragms can be increased. The upper boundary of filter 9 is situated in the plane that is common with the upper boundary of output diaphragm 28 so that only the radiation scattered by the object would fall on the detector.

What is claimed is:

1. A mammography device, comprising a source of a penetrating radiation having a slit collimator, holder of a tested object and position-sensitive detector with an information processing system, characterised in that the detector is provided with a spatial filter designed to extract, on the detector, a reduced-angle coherently scattered radiation, the source with the collimator and the detector with the filter being positioned on a frame, the device being provided with means for relative movement of the frame and object in the plane normal to that of the radiation beam, and for discrete rotation of the frame with fixing of the same in each position relative to the tested object holder.

2. The device as claimed in claim 1, characterised in that the collimator is implemented as a multi-slit collimator, and the spatial filter is implemented in the form of a periodic structure, comprising areas transparent and opaque to radiation, the filter opaque areas carrying elements of the space-sensitive detector intended to register the primary beam of the radiation passed through the object.

3. The device as claimed in claim 1, characterised in that the spatial filter is translucent to the incident radiation.

4. The device as claimed in claim 3, characterised in that the position-sensitive detector is an one-coordinate detector in the form of a linear gas meter.

5. The device as claimed in claim 1, characterised in that the collimator and spatial filter are implemented as a single unit whose entry portion facing the radiation source is a Kratky collimator having input and output diaphragms made in the form of stepped cuts in the unit body; the upper edge of the filter being situated in the plane that is common with the upper edge of the collimator output diaphragm, and between the collimator and filter free space to accommodate an object being provided.

6. A mammography device, comprising a source of a penetrating radiation having a slit collimator, holder of a tested object and position-sensitive detector with an information processing system, characterised in that the detector is provided with a spatial filter intended to extract, on the detector, a reduced-angle scattered radiation, the source with the collimator and the detector with the filter being positioned on a frame provided with means for swinging relative to object holder in the plane normal to that of the radiation beam.

7. A mammography device, comprising a source of a penetrating radiation having a slit collimator, holder of a tested object and position-sensitive detector with an information processing system, characterised in being provided with at least one additional pair of the source with the collimator and the position-sensitive detector, each detector being provided with a spatial filter intended to extract, on the detector, a reduced-angle scattered radiation, each pair being positioned on a frame designed to provide the possibility of movement one after another, toward one another and in two mutually perpendicular directions in the plane normal to that of the radiation beam.

* * * * *